United States Patent
Salamone et al.

(10) Patent No.: US 7,276,347 B2
(45) Date of Patent: Oct. 2, 2007

(54) CYTOXAN ANTIBODIES AND IMMUNOASSAY

(75) Inventors: Salvatore J. Salamone, Stockton, NJ (US); Jodi Blake Courtney, Doylestown, PA (US); Dennis Stocker, Yardley, PA (US)

(73) Assignee: Saladax Biomedical Inc., Bethlehem, PA (US)

( * ) Notice: Subject to any disclaimer, the term of this patent is extended or adjusted under 35 U.S.C. 154(b) by 77 days.

(21) Appl. No.: 11/185,361

(22) Filed: Jul. 20, 2005

(65) Prior Publication Data

US 2006/0024752 A1    Feb. 2, 2006

Related U.S. Application Data

(63) Continuation-in-part of application No. 11/072,910, filed on Mar. 4, 2005.

(60) Provisional application No. 60/592,016, filed on Jul. 29, 2004.

(51) Int. Cl.
- *G01N 33/53* (2006.01)
- *C07K 16/00* (2006.01)
- *C07F 9/09* (2006.01)
- *C07F 9/141* (2006.01)

(52) U.S. Cl. .............. 435/7.93; 530/388.9; 530/389.8; 530/405; 530/406; 558/199

(58) Field of Classification Search ............... 435/7.93; 530/388.9, 389.8, 405, 406, 506; 558/199
See application file for complete search history.

(56) References Cited

OTHER PUBLICATIONS

G. Zon et al, Journal of Medicinal Chemistry (1984), vol. 27, pp. 466-485.*

G. Zon et al, (1982) HCAPLUS abstract accession No. 1982:416494. O-Methylhydroxylamine as a new trapping reagent for quantitative studies of 4-hydroxycyclophosphamide and aldophosphamide.*

S. Ludeman et al, (1985) HCAPLUS abstract accession No. 1995:448403. Oxime Derivatives of the Intermediary Oncostatic Metabolites of Cyclophosphamide and Ifosfamide: Synthesis & Deuterium Labeling for Applications to Metabolite Quantification.*

The International Search Report and Written Opinion of the International Searching Authority by the International Searching Authority, issued on Mar. 7, 2007, in the PCT application No. PCT/US05/25483.

Chen et al., Nonlinear Pharmacokinetics of Cyclophosphamide and 4-Hydroxycyclophosphamide/Aldophosphamide in Patients with Metastatic Breast Cancer Receiving High-dose Chemotherapy Followed by Autologous Bone Marrow Transplantation, 1997, Drug Mutabolism & Disposition, vol. 25, No. 5, pp. 544-551.

Drug Metabolism and Dispositon. 1997, vol. 25, No. 5, pp. 544-551.

* cited by examiner

*Primary Examiner*—Long V. Le
*Assistant Examiner*—Shafiqul Haq

(57) ABSTRACT

Novel conjugates of protected aldehyde active metabolites of cyclophosphamide including reagents and immunogens thereof and monoclonal antibodies generated by these immunogens, said reagents and immunogens useful in immunoassays for the monitoring of the active metabolites of cyclophosphamide in patients being treated with cyclophosphamide.

50 Claims, No Drawings

CYTOXAN ANTIBODIES AND IMMUNOASSAY

CROSS-REFERENCE TO RELATED APPLICATION

This Application is a Continuation-In-Part of application Ser. No. 11/072,910, filed Mar. 4, 2005, which also claims the benefit of Provisional Application Ser. No. 60/592,016, filed Jul. 29, 2004.

FIELD OF THE INVENTION

This invention relates to the field of immunological assays for determining the presence and/or quantifying the amount of active Cytoxan metabolites in human biological samples in order to rapidly determine optimal drug concentrations during chemotherapy.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

Cytoxan is one of the more commonly used cytotoxic agents. This chemotherapeutic agent whose common chemical name is cyclophosphamide has the formula:

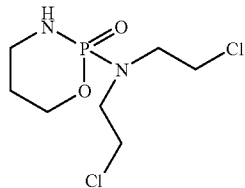

I cyclophosphamide is a pro-drug for administering the active 4-hydroxycyclophosphamide (HCY) which has the formula:

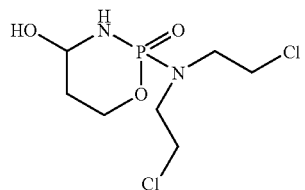

II-A

The compound of Formula I, cyclophosphamide, metabolizes into the compound of formula II-A in the bloodstream when cyclophosphamide is administered to a patient as a therapeutic agent. As active ingredients, the compound of formula II-A exists with its tautomeric form as an aldophosphoramide which has the formula:

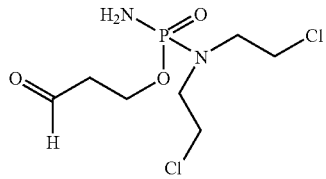

II-B

Both the compounds of formula II-A and its tautomer, the compound of formula II-B while being the active ingredients are unstable compounds outside the bloodstream. Therefore, in order to administer the compound of formula II-A and II-B to patients, these compounds have to be administered as cyclophosphamide.

Since the compound of formula II-A and its tautomer, the compound of formula II-B are unstable, immunoassays to detect their presence are not practical. In order to determine and/or quantitate, by immunoassays, the presence of the compound of formula II-A and/ors it tautomer, the compound of formula II-B, in the bloodstream of a patient, it has been necessary to trap out the active species, i.e., the compound of formula II-A and II-B. This has been done by protecting the aldehyde group on the active species present in the compound of formula II-B by forming a protected aldehyde such as an oxime or hydrazone. The formation of these protecting groups from the aldehyde group of aldophosphamide can be done by conventional means for forming a protected aldehyde group and the presence of the active ingredients in the bloodstream measured from this stable trapped derivative as described by Ludeman et. al. J. Pharma. Sci., 84(4): PP 393-398, 1995, Zon et. al. J. Pharma. Sci., 71(4): pp 443-446, 1982, and McDonald et. al. Blood, 101(5): pp 2043-2048, 2003. By monitoring the levels of the active cyclophosphamide species in the body and adjusting the dose, the side effects resulting to patients from cyclophosphamide administration can be better controlled and limited. (Ren et. al. Clin. Pharmacol. Ther. 64(3): pp 289-301, 1998, et. al.; Petros et. al., Clin. Cancer Res. 8: pp 698-705, 2002; and Chen et. al. Cancer Research 55: pp 810-815, 1995).

Another reason for monitoring is that there is often high variable relationship between the dose of cyclophosphamide administered and the resulting serum drug concentration which varies the therapeutic effect. The degree of intra- and inter-individual pharmacokinetic variability of cyclophosphamide can be as high as 9-fold (Chang et. al. Pharmacogenetics 7: 211-221, 1997, Ren et. al. Clin. Pharmacol. Ther. 64(3): pp 289-301, 1998) and is impacted by many factors, including:
  Organ function
  Genetic regulation
  Disease state
  Age
  Drug-drug interaction
  Time of drug ingestion
  Mode of drug administration, and
  Technique-related administration.

As a result of this variability, equal doses of the same drug in different individuals can result in dramatically different clinical outcomes (Hon et. al. *Clinical Chemistry* 44, pp 388-400, 1998). The effectiveness of the same cyclophosphamide dosage varies significantly based upon individual drug clearance and the ultimate serum drug concentration in the patient. Therapeutic drug management would provide the clinician with insight on patient variation in both oral and intravenous drug administrations. With therapeutic drug management, drug dosages could be individualized to the patient, and the chances of effectively treating the cancer without the unwanted side effects would be much higher (Nieto, Current Drug Metabolism 2: pp 53-66, 2001).

In addition, therapeutic drug management of cyclophosphamide would serve as an excellent tool to ensure compliance in administering chemotherapy with the actual prescribed dosage and achievement of the effective serum concentration levels. It has been found that variability in serum concentration of the active ingredients of cyclophosphamide is not only due to physiological factors, but can also result from variation in administration technique and ability of the body to absorb and metabolize cyclophosphamide. This is especially true given cyclophosphamide, when administered to a patient, is generally absorbed and metabolized into its active ingredients by the patient at different rates. Therefore, in monitoring the level of these active ingredients in patients by means of an immunoassay, it is important that the immunoassay be able to distinguish the active ingredients of the compound of formula II-A and II-B, from the inactive substance of the compound of formula I, i.e., cyclophosphamide. The problem with antibodies to these active ingredients is that they cross-react with cyclophosphamide making these immunoassays not useful.

Routine therapeutic drug management of cyclophosphamide would require the availability of simple automated tests adaptable to general laboratory equipment. Tests that best fit these criteria are immunoassays. Currently there are no immunoassays for cyclophosphamide administration available and monitoring levels of the active metabolites of cyclophosphamide is conducted by physical methods like high pressure liquid chromatography (HPLC) (Escoriaza et. al. J. of Chromatography B: Biomedical Sciences and applications, 736 (1+2): pp 97-102, 1999). In order to be most effective in monitoring drug levels the antibody should be specific to cyclophosphamide metabolites in their stable form and display very low cross-reactivity to no cross-reactivity to related compounds, particularly cyclophosphamide.

SUMMARY OF INVENTION

In accordance with this invention, a new class of antibodies have been produced which are substantially selectively reactive to the stable form of the active cyclophosphamide metabolites of formula II-A and II-B so as to bind to this stable form without any substantial cross reactivity to cyclophosphamide. By selectively reactive it is meant that this antibody reacts with the stable form of the active cyclophosphamide metabolites of formula II-A and II-B and does not substantially react with the cyclophosphamide, and the interfering analogues of cyclophosphamide, the most important being cyclophosphamide. By providing an antibody that does not substantially cross-react with cyclophosphamide, allows one to carry out an immunoassay for the active cyclophosphamide metabolites so as to accurately monitor levels of the presence of these active cyclophosphamide metabolites for therapeutic management of patients being treated with cyclophosphamide.

It has been found that by using immunogens which are conjugates of an immunogenic polyamine polymer with a compound of the formula:

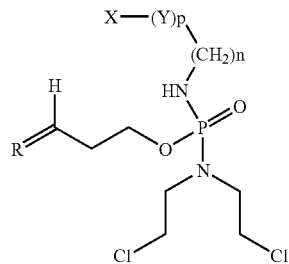

wherein =R forms an aldehyde protecting group;
Y is an organic spacing group;
X is a terminal functional group capable of binding to a polyamine polymer;
p is an integer from 0 to 1, and
n is an integer from 1 to 6 produce antibodies which are specific for the active metabolites of formula II-A and II-B and do not substantially react with cyclophosphamide itself as well as the other interfering analogues of cyclophosphamide. The provision of these antibodies which substantially selectively react with the active metabolites of formula II-A and II-B and do not cross react with cyclophosphamide allows one to produce an immunoassay which can specifically detect and monitor these active metabolites in the fluid samples of patients being treated with cyclophosphamide. Also included within this invention are reagents and kits for said immunoassay. The presence of cyclophosphamide is the major cause for false positive readings which have made immunoassays for the active forms of cyclophosphamide unsuitable.

DETAILED DESCRIPTION

In accordance with this invention, a new class of antibodies is provided which substantially selectively react with the active cyclophosphamide metabolites of formula II-A and II-B and do not substantially react or cross react with cyclophosphamide itself as well as the other interfering analogues of cyclophosphamide. It has been discovered that through the use of the immunogen produced from the compound of formula III, this new class of antibodies of this invention are provided. It is through the use of these antibodies that an immunoassay, including reagents and kits for such immunoassay for detecting and/or quantifying these active cyclophosphamide metabolites in blood, plasma or other body fluid samples has been developed. By use of this immunoassay, the presence and amount of active cyclophosphamide metabolites in body fluid samples, preferably a blood or plasma sample, can be detected and/or quantified. In this manner, a patient being treated with cyclophosphamide can be monitored during therapy and his treatment adjusted in accordance with said monitoring. By means of this invention one achieves the therapeutic drug management of cancer patients being administered with cyclophosphamide as a chemotherapeutic agent.

The reagent utilized in the immunoassay of this invention are conjugates of a carrier with the compound of formula III. For carrying out this immunoassay, this conjugate reagent should contain the identical protecting group R as the protecting group R present in the immunogen used for forming the antibody used in this immunoassay In the immunoassay of this invention, these conjugates are competitive binding partners with the active cyclophosphamide metabolites of formula II-A and II-B present in the sample for the binding with the antibodies of this invention. However, due to the instability of these active cyclophosphamide metabolites, prior to carrying out this immunoassay, these metabolites in the sample are trapped by converting the aldehyde group to a protected aldehyde group. This is accomplished by treating the sample after collection with an agent that will protect the aldehyde group by converting it to an aldehyde protecting group of the formula:

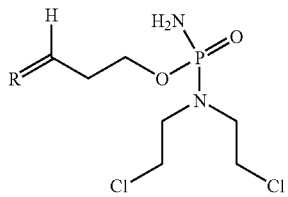

II-C

The compound of formula II-C is the stable form of the compounds of formula II-A and II-B and it is the compound for which one assays to determine the presence of the active cyclophosphamide metabolites of formula II-A and II-B. In trapping the aldehyde of the compound of formula II-B through an aldehyde protecting group R, the identical aldehyde protecting group R used in the carrier conjugate and immunogen should be used for trapping the aldehyde of the sample as the compound of formula II-C for this immunoassay.

In this immunoassay the amount of conjugate reagent which binds to the antibody will be inversely proportional to the amount of these active cyclophosphamide metabolites present in the sample. In accordance with this invention, the assay utilizes any conventional measuring means for detecting and measuring the amount of said conjugate which is bound or unbound to the antibody. Through the use of said means, the amount of the bound or unbound conjugate can be determined. Generally, the amount of active cyclophosphamide metabolites of formula II-A and II-B in a sample is determined by correlating the measured amount of the bound or unbound conjugate produced by the sample with values of the bound or unbound conjugate determined from standard or calibration curve samples containing known amounts of active cyclophosphamide metabolites of formula II-A and II-B, which known amounts are in the range expected for the sample to be tested. These studies for producing calibration curves are determined using the same immunoassay procedure as used for the sample.

The conjugate reagents and immunogens are prepared from the compound of formula III. In the immunogens and carrier, the polyamine polymer or the carrier is linked to the ligand portion which has the formula:

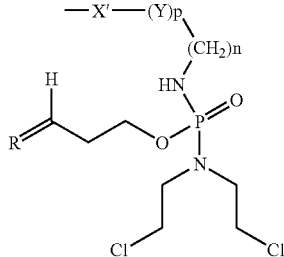

IV wherein Y, R, p and n are as above; and $X'$ is —$CH_2$— or a functional linking group.

Definitions

Throughout this description the following definitions are to be understood:

The terms "immunogen" and "immunogenic" refer to substances capable of eliciting, producing, or generating an immune response in an organism.

The term "conjugate" refers to any substance formed from the joining together of two parts. Representative conjugates in accordance with the present invention include those formed by the joining together of a small molecule, such as the compound of formula II-B, and a large molecule, such as a carrier or a polyamine polymer, particularly protein. In the conjugate the small molecule may be joined at one or more active sites on the large molecule.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is the compound of formula II-C.

As used herein, a "spacing group" or "spacer" refers to a portion of a chemical structure which connects two or more substructures such as haptens, carriers, immunogens, labels, or tracers through a $CH_2$ or functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein, that can join with a hapten, in this case the compound of formula II-C, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also various protein types may be employed as a poly (amino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized.

Immunogenic carriers can also include poly amino-polysaccharides, which are a high molecular weight polymers built up by repeated condensations of monosaccharides. Examples of polysaccharides are starches, glycogen, cellulose, carbohydrate gums such as gum arabic, agar, and so forth. The polysaccharides also contain polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, Strepyococcus, Staphylococcus aureus, E. coli, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 moleculer weight, having no upper moleculer weight limit, normally being less than 10,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" for forming the conjugate with the compound of formula III refers to solid particles and/or polymeric polymers such as immunogenic polymers such as those mentioned above. Where the carrier is a solid particle, the solid particle may be bound, coated with or otherwise attached to a polyamine polymer to provide one or more reactive sites for bonding to the terminal functional group X in the compounds of the formula III.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for the compound of formula II-C. The kit may further comprise ligands of the analyte and calibration and control materials. The reagents may remain in liquid form or may be lyophilized.

The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Reagents and Immunogens

In constructing an immunoassay, a conjugate reagent formed from the compound of formula III is constructed to compete with the compound of formula II-C, formed by trapping the compounds of formulae II-A and II-B in the sample in their stable form, for binding sites on the antibodies of this invention. In the immunoassay of this invention, the immunogen for producing the antibodies of this invention is an immunogen prepared from the compound of formula III, the linker spacer constitutes the —$(CH_2)_n$—$(Y)_p$—X— portion of this molecule. The linker X and the spacer —$(CH_2)_n$—$(Y)_p$—are conventional in preparing conjugates and immunogens. Any of the conventional spacer-linking groups utilized to prepare conjugates and immunogens for immunoassays can be utilized in the compounds of formula III. Such conventional linkers and spacers are disclosed in U.S. Pat. No. 5,501,987 and U.S. Pat. No. 5,101,015.

Among the preferred spacer groups are included the spacer groups hereinbefore mentioned. Particularly preferred spacing groups are groups such as alkylene containing from 1 to 6 carbon atoms,

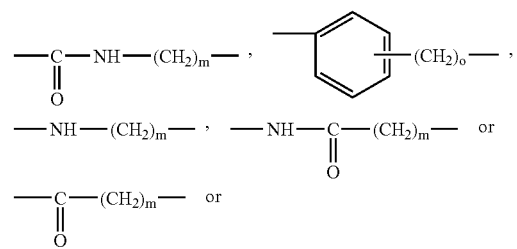

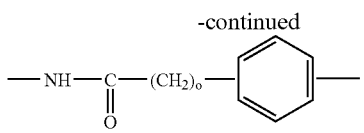

wherein o is an integer from 0 to 6, and m is an integer from 1 to 6 with alkylene being the especially preferred spacing group.

In the ligand portion of formula IV which is connected to the immunogen or carrier, X' is —CH$_2$— or a functional group linking the spacer, preferably to an amine group on the polymer or the carrier or immunogen. The group X' is the result of the terminal functional group X in the compound of Formula III which is capable of binding to the amino group in the polyamine polymer used as either the carrier or the immunogen. Any terminal functional group capable of reacting with an amine can be utilized as the functional group X in the compound of formula III. These terminal functional groups preferably included within X are:

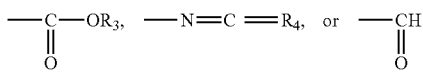

wherein R$_3$ is hydrogen or taken together with its attached oxygen atom forms a reactive ester and R$_4$ is oxygen or sulfur, the radical 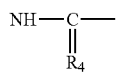 can be an isocyanate or as isothiocyanate. The active esters formed by OR$_3$ include imidoester, such as N-hydroxysuccinamide, 1-hydroxy benzotriazole and p-nitrophenyl ester. However any active ester which can react with an amine group can be used.

The carboxylic group and the active esters are coupled to the carrier or immunogenic polymer by conventional means. The amine group on the polyamine polymer, such as a protein, produces an amide group which connects the spacer to the polymer, immunogens or carrier and/or conjugates of this invention.

In the immunogens and conjugates of the present invention, the chemical bonds between the carboxyl group-containing haptens of the compound of formula III and the amino groups on the polyamine polymer on the carrier or the immunogen can be established using a variety of methods known to one skilled in the art. It is frequently preferable to form amide bonds. Amide bonds are formed by first activating the carboxylic acid moiety of the hapten in the compounds of formula III by reacting the carboxyl group with a leaving group reagent (e.g., N-hydroxysuccinimide, 1-hydroxybenzotriazole, p-nitrophenol and the like). An activating reagent such as dicyclohexylcarbodiimide, diisopropylcarbodiimide and the like can be used. The activated form of the carboxyl group in the hapten of formula III is then reacted with a buffered solution containing the protein carrier.

In cases where the hapten derivative of formula III contains a primary or secondary amino group as well as the carboxyl group, it is necessary to use an amine protecting group during the activation and coupling reactions to prevent the conjugates from reacting with themselves. Typically, the amines on the conjugate are protected by forming the corresponding N-trifluoroacetamide, N-tertbutyloxycarbonyl urethane (N-t-BOC urethane), N-carbobenzyloxy urethane or similar structure. Once the coupling reaction to the immunogenic polymer or carrier has been accomplished, as described above, the amine protecting group can be removed using reagents that do not otherwise alter the structure of the immunogen or conjugate. Such reagents and methods are known to one skilled in the art and include weak or strong aqueous or anhydrous acids, weak or strong aqueous or anhydrous bases, hydride-containing reagents such as sodium borohydride or sodium cyanoborohydride and catalytic hydrogenation. Various methods of conjugating haptens and carriers are also disclosed in U.S. Pat. No. 3,996,344 and U.S. Pat. No. 4,016,146, which are herein incorporated by reference.

On the other hand where X is a terminal isocyanate or thioisocyanate radical in the compound of formula III, these radicals when reacted with the free amine of a polyamine polymer produce the conjugate of formula IV or the immunogen where X' is

where R$_4$ is as above, which functionally connects with the amino group on the polyamine carrier or the immunogenic polypeptide.

Where X, in the compounds of formula III, is an aldehyde group these compounds may be connected to the amine group of the polyamine polypeptide or carrier through an amine linkage by reductive amination. Any conventional method of condensing an aldehyde with an amine such as through reductive amination can be used to form this linkage. In this case, X' in the ligand portions of formula IV is —CH$_2$—.

In accordance with this invention any conventional method of forming an aldehyde protecting group can be used to convert the compound of formula II-A and II-B to the compound of formula II-C. In accordance with this invention, R can form a conventional aldehyde protecting group. Among the preferred aldehyde protecting groups are included acetals and cyclic acetels, that is where —CH=R in the compound of formula II-B is:

$$-\text{CH} \diagup^{OR_5}_{OR_6}$$

where R$_5$ and R$_6$ are identical lower alkyl groups or taken together form a lower alkylene bridge containing from 2 to 6 carbon atoms.

Another preferred group of aldehyde protecting groups which can be formed by R in accordance with this invention are the alkyl hydrazones and phenyl hydrazones such as 2,4-dinitrophenyl hydrazones, the oximes and the semicarbazones. With respect to the hydrazones, the —CH=R portion of the compound of formula II-C forms a radical of the formula:

where $R_{17}$ is phenyl, substituted phenyl, lower alkyl or

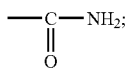

and $R_{18}$ is hydrogen or lower alkyl.

When the aldehyde protecting group in the compound of formula II-C is an oxime the —CH=R portion of the compound of formula II-C forms a radical of the formula:

where $R_8$ is lower alkyl.

Any conventional method of converting an aldehyde group into one of the protecting groups can be used in converting the aldehyde group in the compound of formula II-B so that the compound of formula II-A and II-B is trapped as the compound of formula II-C.

The compound of formula III can be prepared from the compound of the formula:

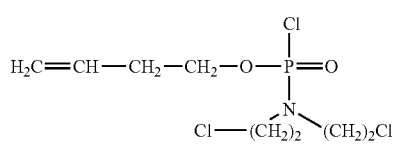

V

In preparing the compound of formula III the compound of formula V is first reacted with a compound of the formula:

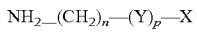 VI wherein n, X, Y and p are as above to produce the compound of the formula:

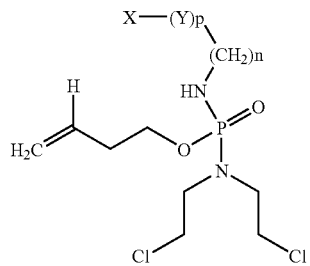 VII

The compound of formula VII is next converted to a compound of the formula:

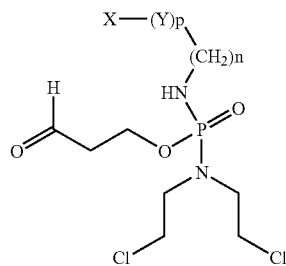 VIII where X, Y, p and n are as above.

The reaction of the compound of formula V with the compound of formula VI can be carried out utilizing any conventional means of condensing an amine with a chloride. In this synthesis the phosphochloride is more reactive than the other chlorine groups on the ethylene chloride moieties attached to the nitrogen atom. Therefore, the phosphorohalide quickly reacts with the amine group on the compound of formula VI. In carrying out this reaction, the reactive functional groups which may be present in the substituents represented by X and Y are protected by means of various protecting groups which can be removed at a subsequent step in this reaction scheme. In this manner, the compound of formula VII is produced. The compound of formula VII can be converted to the compound of formula VIII by oxidizing the double bond to an aldehyde substituent. Any conventional method of converting a double bond into an aldehyde can be utilized to carry out this reaction. Among the preferred methods of oxidation are ozonalysis. Any conventional method of ozonalysis can be utilized. The aldehyde on the compound of formula VIII can be converted to the compound of formula III by converting the aldehyde into an aldehyde protecting group. Any of the conventional aldehyde protecting groups can be utilized in this procedure. In forming the compound of formula III, in its stable condition, this compound contains the aldehyde as a protected aldehyde group.

In accordance with this invention, any conventional method of protecting an aldehyde and any conventional aldehyde protecting group, can be used to protect the free aldehyde in the compound of formula VIII to produce the compound of formula III or the free aldehyde group in the compound of formula II-B. Among the preferred methods is to produce hydrazones by reacting the compound of formula VIII or the compound of formula II-B with the compound of the formula:

 X wherein $R_7$ is lower alkyl, phenyl or substituted phenyl; and $R_9$ is hydrogen or lower alkyl.

The compound of formula III and II-C where =R forms a hydrazone can be produced by reacting the compound of formula VIII and II-B with the compound of formula X. Any conventional method of converting an aldehyde to a hydrazone can be used in this conversion. The term lower alkyl is used herein to denote monovalent alkyl groups containing from 1 to 7 carbon atoms such as methyl, ethyl, propyl, isobutyl, pentyl, etc. The term substituted phenyl denotes a phenyl moiety substituted in from 1 to 3 positions, preferably 1-2 positions with a nitro or halo substituted, especially preferred is 2,4-dinitro substituted phenyl.

Another preferred protecting groups are oximes. These are formed by reacting the free aldehyde group in the compound of formula II-B and VIII with a compound of the formula:

 XI wherein $R_8$ is a lower alkyl.

These oximes are formed by utilizing conventional means for converting free aldehydes into oximes.

On the other hand, the free aldehydes in the compounds of formula VIII and II-B can be converted into semicarbazones, i.e., wherein:

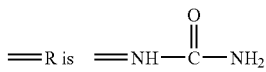 XII by reacting with a compound of the formula:

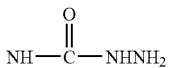

XIII utilizing conventional means for converting aldehydes into semicarbazones.

Another preferred protecting group is the acetal group, i.e., wherein =R is:

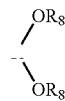

XIV wherein $R_8$ and $R_8$ are as above; or which are prepared by reacting the compound of formula II-B or VIII with an aldehyde of the formula:

     XV wherein $R_8$ is as above.

utilizing conventional means for converting aldehydes to acetals.

Another preferred aldehyde protecting group is cyclic acetals, i.e., wherein =R is:

XVI wherein $R_{11}$ is lower alkylene which are prepared by reacting the compound of formula VIII or II-B with a diol of the formula:

     XVII wherein $R_{11}$ is as above utilizing conventional means for converting a free acetal into a cyclic acetal.

The Term lower alkylene designates a divalent saturated hydrocarbon having from 2 to 7 carbon atoms, preferably with the divalent bond placed on two different carbon atoms, such as 1,2 ethylene; 1,3 propylene; 1,4 butylene, etc.

The compound of formula III can be converted into the immunogens with the conjugate carrier reagent of this invention by reacting these compounds with a polyamine, polypeptide or a carrier. The same polypeptide can be utilized as the carrier in the immunogen provided that the polyamine or polypeptide is immunologically active.

However, to form the conjugates, these polymers need not produce an immunological response as needed for the immunogens. In accordance with this invention, the various functional groups represented by X in the compound of formula III can be conjugated to the polymeric material by conventional means of attaching a functional group to an amine group contained within the polymer. In accordance with a preferred embodiment, in the compound of formula III, X is a carboxylic acid group or active esters thereof.

Antibodies

The present invention also relates to novel antibodies including monoclonal antibodies to the stable form of the active cyclophosphamide metabolites of formula II-C. These antibodies are produced by utilizing the aforementioned immunogens. In accordance with this invention it has been found that these antibodies produced in accordance with this invention are selectively reactive with the stable form of the compounds of formula II-A and II-B and do not react with cyclophosphamide or other cyclophosphamide analogs which would interfere with immunoassays.

The present invention relates to novel antibodies and monoclonal antibodies to the stable form of the active cyclophosphamide metabolites of formula II-C. The antisera of the invention can be conveniently produced by immunizing host animals with the immunogens of this invention. Suitable host animals include rodents, such as, for example, mice, rats, rabbits, guinea pigs and the like, or higher mammals such as goats, sheep, horses and the like with mice, rats and rabbits being especially preferred. Initial doses, bleedings and booster shots can be given according to accepted protocols for eliciting immune responses in animals, e.g., in a preferred embodiment mice received an initial dose of 100 ug immunogen/mouse, i.p. and one or more subsequent booster shots of 100 ug immunogen/mouse over a six month period. Through periodic bleeding, the blood samples of the immunized mice were observed to develop an immune response against the compound of formula II-C binding utilizing conventional immunoassays. These methods provide a convenient way to screen for hosts which are producing antisera having the desired activity.

Monoclonal antibodies are produced conveniently by immunizing Balb/c mice according to the above schedule followed by injecting the mice with 100 ug immunogen i.p. or i.v. on three successive days starting three days prior to the cell fusion. Other protocols well known in the antibody art may of course be utilized as well. The complete immunization protocol detailed herein provided an optimum protocol for serum antibody response for the antibody to the stable form of the active cyclophosphamide metabolites of formula II-C.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that which imparts long term tissue culture stability on the hybrid cell. In the preferred embodiment of the invention the immortal cell may be a lymphoblastoid cell or a plasmacytoma cell such as a myeloma cell, itself an antibody producing cell but also malignant. Murine hybridomas which produce these monoclonal antibodies of this invention are formed by the fusion of mouse myeloma cells and spleen cells from mice immunized against protein conjugates of the compound of formula III. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO 92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutagenesis to produce Fab fragments or (Fab')$_2$ fragments. Single chain antibodies may be produced by joining VL and VH regions with a DNA linker (see Huston et al., *Proc. Natl. Acad. Sci. U.S.A.*, 85:5879-5883 (1988) and Bird et al., *Science*, 242:423-426 (1988))

The antibodies of this invention are selective for the stable form of the active cyclophosphamide metabolites of formula II-C and do not have any substantial cross-reactivity with such cyclophosphamide or other cyclophosphamide analogues. By having no substantial cross-reactivity it is meant that the antibodies of this invention have a cross reactivity relative to the stable form of the active cyclophosphamide metabolites of formula II-C with cyclophosphamide or the other cyclophosphamide analogues of not greater than 10%, preferably less than 5%.

Immunoassays

In accordance with this invention, the conjugate of the carrier with the compound of formula III, together with the antibody generated from the immunogens formed from the immunogenic proteins conjugated with the compound of formula III can be utilized as reagents for determining the presence of the active metabolites of cyclophosphamide in patient samples. In forming these reagents the R group that was present in the immunogen used to form the antibody should be the same as in the conjugate of the carrier with the compound of formula III used as the reagent in the immunoassay.

In first carrying out this immunoassay, the sample is treated in such a manner so as to protect the free aldehyde in the free aldehyde metabolite of formula II-B present in the sample in the form of the compound of formula II-C. Any means for treating the free aldehyde present in the cyclophosphamide metabolite of formula II-B can be utilized to carry out this treatment procedure. Among the preferred methods are the conventional methods of the prior art such as described herein before. In this manner, the free aldehyde of the active metabolites which may be present in the sample are protected so that the metabolites are stable. By converting the free metabolites of formula II-B to the protected metabolites of formula II-C, the tautomer of formula II-A is converted into its other tautomer by means of the fact that both tautomers exist in equilibrium so that upon this treatment the tautomer of formula II-A is converted via the tautomer of formula II-B to the protected aldehyde of formula II-C.

Once the sample is treated in the foregoing manner, the treated sample is subjected to an immunoassay for determining the presence and/or quantitating the active metabolites of cyclophosphamide that may be present in the sample. Any conventional immunoassay in which the reagent conjugate formed from a carrier with the compound of formula III compete with the stabilized active cyclophosphamide metabolite of formula II-A in the sample, for binding sites on the antibody generated in accordance with this invention can be utilized to determine the presence of and/or quantitate the active metabolites of cyclophosphamide, i.e., the compounds of formula II-A and/or II-B in the patient sample. The manner for conducting such an assay for the active cyclophosphamide metabolites in the sample suspected of containing these active metabolites comprises combining in an aqueous medium a) the sample which has been treated to protect the free aldehyde group present in the active cyclophosphamide metabolites; b) an antibody to the compound of formula II-C generated in accordance with this invention; and c) the reagent which is a conjugate of the carrier with the compound of formula III. In carrying out this immunoassay it is important the aldehyde protecting groups in both the compound of formula III used to form the reagent and the antibody be the same as that used to protect the free aldehyde active cyclophosphamide metabolite which may be present in the sample.

The amount of the active metabolites of cyclophosphamide can be determined through the use of the compound of Formula II-C in the treated sample, by measuring the amount of inhibition of the binding to the specific antibody of a known amount of the conjugate reagent, added to the mixture of the sample and antibody. The result of the inhibition of such binding of the known amount of conjugate reagent by the unknown sample is compared to the results obtained in the same assay by utilizing known standard solutions of known amounts containing the active cyclophosphamide metabolites in the form of the compound of formula II-C. In determining the amount of the active cyclophosphamide metabolites in an unknown sample, the sample which is treated to convert the compounds of formula II-A and II-B to the compound of formula II-C, the reagent which is the conjugate formed from the compounds of formula III and the antibody may be added in any order.

Various means can be utilized to measure the amount of the added reagent conjugate formed from the compounds of formula III bound to the antibody. One method is where binding of the added reagent conjugate to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. Nos. 4,269,511 and 4,420,568.

On the other hand, the antibody can be coated or absorbed on nanoparticles so that when these particles react with the added reagent conjugates formed from the compounds of formula III, these nanoparticles form an aggregate. However, when the antibody coated or absorbed nanoparticles react with the compound of formula II-C in the sample, the formula II-C from the sample bound to these nanoparticles does not cause aggregation of the antibody nanoparticles. The amount of aggregation or agglutination can be measured in the assay mixture by absorbance.

On the other hand, these assays can be carried out by having either the antibody or the reagent conjugates attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the reagent conjugates formed from the compounds of formula III which is bound or unbound with the antibody. Other suitable labels include chromophores, fluorophores, etc.

As a matter of convenience, assay components of the present invention can be provided in a kit, a packaged combination with predetermined amounts of reagents employed in assaying for the compound of formula II-C. These reagents include the antibody of this invention, as well as, the conjugates reagents formed from the compounds of formula III. The kit can also contain as an additional reagent, a reactant for reacting with a free aldehyde to form the same aldehyde protecting group R in the ligand of formula III which forms the conjugate reagent and which forms the immunogen used to generate the antibody reagent.

In addition to these necessary reagents, additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

EXAMPLES

In the examples, the following abbreviations are used for designating the following:

| HCY | 4-hydroxycyclophosphamide |
|---|---|
| HCY Oxime | O-methyloxime of aldophosphamide |
| DMF | Dimethylformamide |
| EA | Ethyl alcohol |
| DCM | Dichloromethane |
| DMAP | Dimethylaminopyridine |
| DMSO | Dimethylsulfoxide |
| $POCl_3$ | Phosphorus Oxychloride |
| NHS | N-hydroxy succinimide |
| EDC | 1-(3-dimethylaminopropyl)-3-ethylcarbodiimide hydrochloride |
| DCC | Dicyclohexyl carbodiimide |
| TLC | Thin Layer Chromatrography |
| ANS | 8-Anilino-1-naphthalenesulfonic acid |
| i.p. | Intraperitoneal |
| HRP | horse radish-peroxidase |
| TMB | 3,3',5,5'-Tetramethylbenzidine |
| TRIS | Tris(hydroxymethyl)aminomethane hydrochloride |
| BSA | Bovine serum albumin |
| KLH | Keyhole Limpet Hemocyanin |
| BTG | Bovine thyroglobulin |
| PBS | Phosphate buffered saline |
| di | deionized water |

In the examples, Scheme 1 and Scheme 2 of the provisional patent set forth the specific compounds prepared and referred to by numbers in the Examples. These schemes are as follows:

Scheme 1

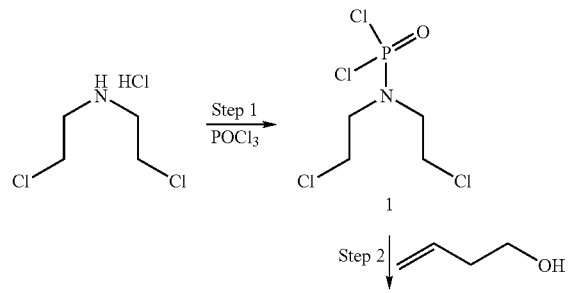

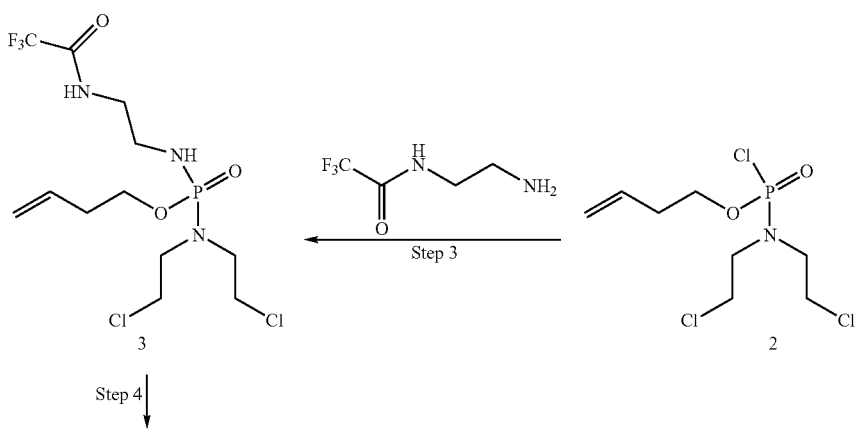

-continued
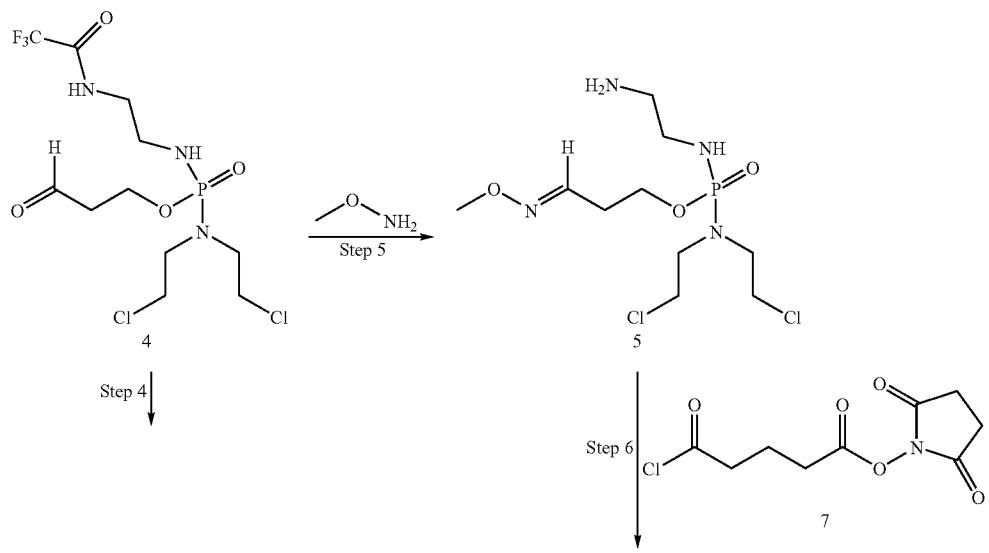
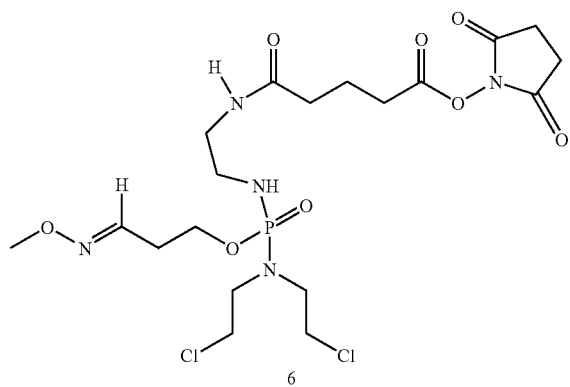
Scheme 2
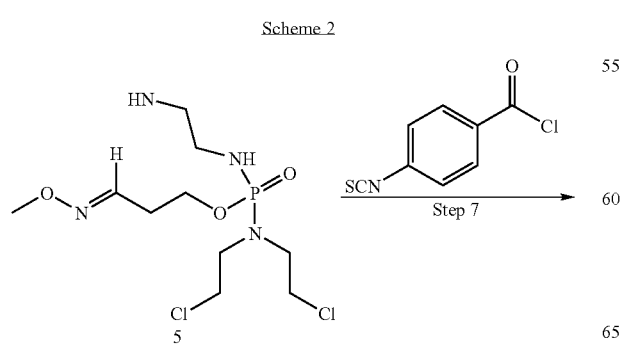
-continued
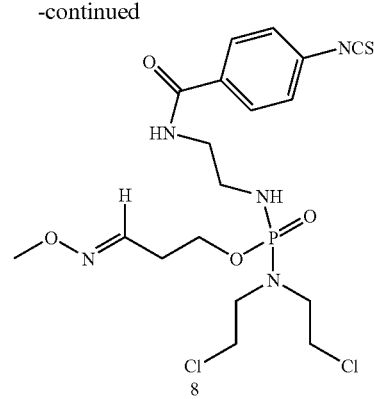

Example 1

Preparation of HCY Oxime Activated Ester 6 (Scheme 1)

N-Butyllithium (8.8 mL, 22.0 mmol) was added drop wise to 3-buten-1-ol (1.44 g, 20.0 mmol) in THF (100 mL) at room temperature, and the solution was stirred for 30 min and then cooled to 0° C. A solution of phosphoramidic chloride [1] (5.44 g, 21.0 mmol) in THF (50 mL) was added rapidly, and the stirring was continued for 1 hour. A solution of N-(2-aminoethyl)-2,2,2,-trifluoroacetamide in THF (80 mL) was added drop wise over 30 min. The reaction mixture was warmed to room temperature, and stirring was continued overnight. The precipitated salts were removed by filtration through Celite, and the filtrate was concentrated. The crude product was purified by flash chromatography (ethyl acetate/hexanes; 50, 60, and 65%) to give [3] (3.35 g, 40%) as a colorless oil.

A solution of [3] (3.35 g, 8.08 mmol) in CH$_2$Cl$_2$ (50 mL) was cooled to −78° C. (dry ice/acetone bath), and ozone was bubbled through the solution until a blue color was evident (ca. 25 min). Excess ozone was flushed from the solution with nitrogen, and the ozonide was reduced by addition of dimethyl sulfide (713 µL, 9.70 mmol). The solution was warmed to −30° C., triethylamine was added (1.64 mL 20.2 mmol) and then methoxyamine hydrochloride (1.48 g, 17.78 mmol). The reaction mixture was warmed to room temperature, and stirring was continued for 3 hours. The mixture was filtered, the filtrate concentrated and the resulting oil was purified by flash chromatography (ethyl acetate/hexanes, 3:2) to give the TFA protected precursor of [5] (1.86 g, 52%) as a thick colorless oil. A solution of this product (603 mg, 1.36 mmol) in NH$_3$ in MeOH (30 mL, ~10 M) and aqueous NH$_3$ (30 mL, 30%) was stirred overnight. The mixture was concentrated. The resulting amine [5] was azeotroped with toluene to remove traces of water. Crude [5] was obtained as yellow oil and was used in the next step without purification.

The above crude [5] and triethylamine (0.378 mL, 2.72 mmol) in THF (10 mL) was added drop wise to a solution of [7] (0.494 g, 1.77 mmol) in THF (20 mL) at 0° C. The reaction was warmed to room temperature and was stirred for 2 hours. The mixture was filtered, washed with dry ether and the filtrate was concentrated. The crude product was further purified by filtration through a small plug of silica with ethyl acetate to give [6] (0.528 g, 69%) as a colorless gum.

Example 2

Preparation of HCY Oxime Isothiocyanate 8 (Scheme 2)

Crude [5] (prepared from 603 mg (1.36 mmol) of the TFA protected precursor) and triethylamine (0.378 mL, 2.72 mmol) in THF (10 mL) was added drop wise to a solution of 4-isothiocyanatobenzoyl chloride (0.404 g, 2.04 mmol) in THF (20 mL) at 0° C. The reaction was warmed to room temperature and was stirred for 2 hours. The mixture was filtered, washed with dry ether and the filtrate was concentrated. The crude product was purified by flash chromatography (ethyl acetate/hexanes 9:1) to give [8](0.528 g, 76%) as a yellow gum.

Example 3

Preparation of HCY Oxime

The HCY oxime was prepared according to the literature procedure (Borch, R. F.; Valente, R. R. *J. Med. Chem.* 1991, 34(10), 3052-3058). The product was isolated in 44% yield.

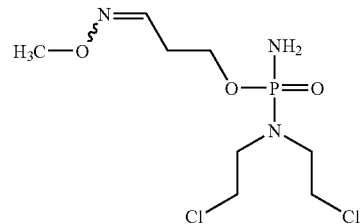

Example 4a

Preparation of BTG Immunogen with Activated Hapten 6

To 6.06 mL of BTG (32.9 mg/mL) in 50 mM phosphate buffer (50 mM, pH 7.5) 1.0 mL of compound [6] (33 mg/mL in DMSO), that was prepared in Example 1, was added drop wise and the pH was again checked to be 7.5. The mixture was allowed to stir 18 hours at room temperature. This immunogenic conjugate was then purified by dialysis (10% DMSO-phosphate buffer for the first dialysis and pure buffer for subsequent changes) and characterized according to procedures described previously (Wu et. al., Bioconj. Chem., 8: pp 385-390, 1997, Li et al., Bioconj. Chem., 8: pp 896-905, 1997, Salamone et al., J. Forensic Sci. pp 821-826, 1998).

Example 4b

Preparation of KLH Immunogen with Activated Hapten 6

To 6.5 mL of KLH (9 mg/mL) in 50 mM phosphate buffer (50 mM, pH 7.5) 0.29 mL of compound [6] (33 mg/mL in DMSO), that was prepared in Example 1, was added drop wise and the pH was again checked to be 7.5. The mixture was allowed to stir 18 hours at room temperature. This immunogenic conjugate was then purified by dialysis (10% DMSO-phosphate buffer for the first dialysis and pure buffer for subsequent changes) and characterized according to procedures described previously (Wu et. al., Bioconj. Chem., 8: pp 385-390, 1997, Li et al., Bioconj. Chem., 8: pp 896-905, 1997, Salamone et al., J. Forensic Sci. pp 821-826, 1998).

Example 5

Preparation of BSA Conjugate (1:1 Ratio) with Activated Hapten 8

To a 20 mL solution of BSA (50 mg/mL) in 50 mM phosphate buffer (50 mM, pH 7.5). the activated isothiocyanate [8] prepared as in example 2 (0.258 mL of a 33 mg/mL in DMSO solution) was added drop wise. The mixture was allowed to stir overnight (18 hours) at room temperature to produce the 1:1 plate conjugate for screening purposes. This conjugate was then purified by dialysis (10% DMSO-phosphate buffer for the first dialysis and pure buffer for subsequent changes) and characterized according to procedures described previously (Wu et al., Bioconj. Chem., 8: pp 385-390, 1997, Li et al., Bioconj. Chem., 8: pp 896-905, 1997, Salamone et al., J. Forensic Sci. pp 821-826, 1998).

Example 6

Preparation of HCY Oxime Antibodies

Ten Female BALB/c mice were immunized i.p. with 100 µg/mouse of HCY Oxime-BTG or HCY Oxime-KLH immunogen prepared in examples 4a & b emulsified in Complete Freund's Adjuvant. Mice were boosted once four weeks after the initial injection with 100 µg/mouse of the same immunogens emulsified in Incomplete Freund's Adjuvant. Ten days after the boost test bleeds from each mouse were obtained by orbital bleed. The anti-serum from these test bleeds contained HCY oxime antibodies evaluated in Examples 8a and 9. For monoclonal antibodies starting four days before the fusion, the mice were injected i.p. with 100 µg of HCY Oxime-BTG or HCY Oxime-KLH (according to the primary injection) in PBS on three successive days. Spleen cells were isolated from the selected mice and fused with $2 \times 10^7$ SP2/0 cells with 50% polyethylene glycol 1500 according to the method of Coligan, J. E. et al., eds., *Current Protocols in Immunology*, 2.5.1-2.5.8, (1992), Wiley & Sons, NY. The fused cells were plated on 10 96-well plates in DMEM/F12 supplemented with 20% FetalClone I, 2% L-glutamine (100 mM) and 2% 50×HAT. Two weeks later, the hybridoma supernatant was assayed for the presence of anti-HCY Oxime antibodies by ELISA (example 8b). Positive wells were expanded and again screened by the same method. The positive clones were confirmed for HCY Oxime binding by a competitive ELISA (examples 8a and 9). Clones positive by ELISA were subcloned once or twice by limiting dilution according to the smethod disclosed in Coligan, J. E. et al., eds., *Current Protocols in Immunology*, 2.5.8-2.5.17, (1992), Wiley & Sons, NY.

Example 7

Microtiter Plate Sensitization Procedure with HCY Oxime Derivative 6 —BSA Conjugate The ELISA method for measuring HCY Oxime concentrations was performed in polystyrene microtiter plates (Nunc MaxiSorp C8 or F8 Immunomodules) optimized for protein binding and containing 96 wells per plate. Each well was coated with HCY Oxime-BSA conjugate (prepared as in example 5) by adding 300 µL of HCY Oxime-BSA conjugate at 1.25 µg/mL (table 1) or 5 ug/mL (table 2) in 0.05M sodium bicarbonate, pH=9.6, and incubating for three hours at room temperature. The wells were washed with 0.05M sodium bicarbonate, pH 9.6 and then were blocked with 400 µL of 5% sucrose, 0.2% sodium caseinate solution for 30 minutes at room temperature. After removal of the post-coat solution the plates were dried at 37° C. overnight.

Example 8a

Antibody Screening Procedure—Titer

The ELISA method for screening HCY Oxime antibodies (produced in example 6) was performed with the microtiter plates that were sensitized with HCY Oxime-BSA as described in example 5. The antibody screening assay was performed by diluting the antisera containing HCY Oxime antibodies to 1:100, 1:1,000, 1:10,000 and 1:100,000 in phosphate buffered saline containing 0.1% BSA and 0.01% thimerosal. For evaluation of monoclonal antibodies, hybridoma supernatants, of Example 6 found to be positive for presence of antibodies by the procedure of Example 8b, were diluted 1:2, 1:4, 1:8, 1:16, etc. To each well of HCY Oxime-BSA sensitized wells (prepared in example 7) 100 µL of diluted antibody was added and incubated for 10 minutes at room temperature with shaking. During this incubation antibody binds to the HCY Oxime-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of HCY Oxime antibody bound to the HCY Oxime-BSA conjugate in the wells, 100 µL of a goat anti-mouse antibody—HRP enzyme conjugate (Jackson Immunoresearch) diluted 1/2400 in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to HCY Oxime antibodies in the wells, the plates were again washed three times to remove unbound goat anti-mouse antibody—HRP enzyme conjugate. To develop a measurable color in the wells washing was followed by the addition of 100 µL of TMB (TMB Liquid Substrate, Sigma), a substrate for HRP, to develop color during a 10 minute incubation with shaking at room temperature. Following the incubation for color development, 50 µL of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured and was expressed as the dilution (titer) resulting in an absorbance of 1.5. Titers were determined by graphing log antibody dilution of the antibody measured (x-axis) vs. absorbance 650 nm (y-axis) and extrapolating the titer at an absorbance of 1.5. The titer determined the concentration (dilution) of antibody used in the indirect competitive Microtiter plate assay described in example 9.

Example 8b

Antibody Screening Procedure—Monoclonal Screening

The ELISA method for screening HCY Oxime monoclonal antibodies (produced in example 6) was performed with the microtiter plates that were sensitized with HCY Oxime-BSA as described in example 5. To each well of HCY Oxime-BSA sensitized wells (prepared in example 7) 50 uL phosphate buffered saline containing 0.1% BSA and 0.01% thimerosal and then 50 µL of monoclonal culture supernatant were added and incubated for 10 minutes at room temperature with shaking. During this incubation antibody binds to the HCY Oxime-conjugate in the well. The wells of the plates were washed three times with 0.02 M TRIS, 0.9% NaCl, 0.5% Tween-80 and 0.001% Thimerosal, pH 7.8 to remove any unbound antibody. To detect the amount of HCY Oxime antibody bound to the HCY Oxime-BSA conjugate in the wells, 100 µL of a goat anti-mouse antibody—HRP enzyme conjugate (Jackson Immunoresearch) diluted 1/2400 in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to HCY Oxime antibodies in the wells, the plates were again washed three times to remove unbound goat anti-mouse antibody—HRP enzyme conjugate. To develop a measurable color in the wells washing was followed by the addition of 100 μL of TMB (TMB Liquid Substrate, Sigma), a substrate for HRP, to develop color during a 10 minute incubation with shaking at room temperature. Following the incubation for color development, 50 μL of stop solution (1.5% sodium fluoride in di H$_2$O) was added to each well to stop the color development and after 10 seconds of shaking the absorbance was determined at 650 nm (Molecular Devices Plate Reader). The amount of antibody in a well was proportional to the absorbance measured. Samples with an absorbance of greater than twice background were designated as positive.

Example 9

Indirect Competitive Microtiter Plate Immunoassay Procedure Determining IC$_{50}$ and Cross-Reactivity for Antibodies to HCY Oxime Derivative 6 Conjugate The ELISA method for measuring HCY Oxime concentrations was performed with the microtiter plates that were sensitized with HCY Oxime-BSA described in example 5. HCY Oxime, cyclophosphamide, chlorambucil, melphalan and mechlorethamine were diluted 10 fold in PBS over a concentration range of 0.01 to 10,000 ng/mL or 100,000 ng/mL. The assay was performed by incubating 50 μL of the analytes to be measured with 50 μL of antibody (produced in example 6 with immunogen of examples 4a and 4b) diluted to a titer determined in example 8a. During the 10 minute incubation (R.T., with shaking) there is a competition of antibody binding for the HCY Oxime conjugate in the well and the analyte in solution. Following this incubation the wells of the plate were washed three times with 0.02 M TRIS, 0.9% NaCl, 0.5% Tween-80 and 0.001% Thimerosal, pH 7.8 to remove any material that was not bound. To detect the amount of HCY Oxime antibody bound to the HCY Oxime-BSA conjugate in the wells, 100 μL of a goat anti-mouse antibody—HRP enzyme conjugate (Jackson Immunoresearch) diluted 1/2400 in PBS with 0.1% BSA, 0.05% ANS, 0.01% thimerosal, capable of binding specifically with murine immunoglobulins and producing a colored product when incubated with a substrate, were added to each well. After an incubation of 10 minutes at room temperature with shaking, during which the goat anti-mouse antibody—HRP enzyme conjugate binds to HCY Oxime antibodies in the wells, the plates were again washed three times to remove unbound secondary conjugate. To develop a measurable color in the wells washing was followed by the addition of 100 μL of TMB (TMB Liquid Substrate, Sigma), a substrate for HRP, to develop color in a 10 minute incubation with shaking at room temperature. Following the incubation for color development, 50 μL of stop solution (1.5% sodium fluoride in di H$_2$O) was added to each well to stop the color development and after 10 seconds of shaking the absorbance was determined at 650 nm (Molecular Devices Plate Reader). The amount of antibody in a well was proportional to the absorbance measured and inversely proportional to the amount of HCY Oxime in the sample. The absorbance of the color in the wells containing analyte was compared to that with no analyte and a standard curve was generated. The IC$_{50}$ value for a given analyte was defined as the concentration of analyte that is required to inhibit 50% of the absorbance for the wells containing no analyte. The cross-reactivity of a given analyte was calculated as the ratio of the IC$_{50}$ for HCY Oxime to the IC$_{50}$ for cyclophosphamide, chlorambucil, melphalan and mechlorethamine expressed as a percent. When measured with an antibody as produced in example 6 with immunogen of example 4a & b the percent cross-reactivates relative to HCY Oxime for cyclophosphamide, chlorambucil, melphalan and mechlorethamine were less than 1%. Results are in table 1 and 2 below.

TABLE 1

Cross-Reactivity of Competitive Immunoassay using antibodies to HCY Oxime-BTG (example 4a) with plate coating HCY Oxime-BSA conjugate (example 5).

| Analyte | IC 50 | % Cross-Reactivity |
|---|---|---|
| HCY Oxime | 30 ng/ml | 100% |
| cyclophosphamide (Prodrug) | >10,000 ng/ml | <0.3% |
| Chlorambucil | >10,000 ng/ml | <0.3% |
| Melphalan | >10,000 ng/ml | <0.3% |
| Mechlorethamine | >10,000 ng/ml | <0.3% |

TABLE 2

Cross-Reactivity of Competitive Immunoassay using a monoclonal antibody to HCY Oxime-KLH (example 4b) with plate coating HCY Oxime-BSA conjugate (example 5).

| Analyte | IC 50 | % Cross-Reactivity |
|---|---|---|
| HCY Oxime | 100 ng/ml | 100% |
| cyclophosphamide (Prodrug) | >100,000 ng/ml | <0.1% |
| Chlorambucil | >100,000 ng/ml | <0.1% |
| Melphalan | >100,000 ng/ml | <0.1% |
| Mechlorethamine | >100,000 ng/ml | <0.1% |

The compounds chlorambucil, melphalan and mechlorethamine, like cyclophosphamide, are all chemotherapeutic drugs which contain in their structure the mustard radical ie a radical containing an amine di-substituted with a chloroethyl substituent. As seen from this table, the antibodies of this invention are substantially selectively reactive with the stable form of the active metabolites of cyclophosphamide and are not substantially cross-reactive with cyclophosphamide and the other cyclophosphamide analogues which contain an amine which is di-substituted with a chloroethyl substituent.

What is claimed is:
1. An immunoassay for detecting in a sample the presence of the active metabolites of cyclophosphamide, which can exist in the form of a free aldehyde containing compound of the formula:

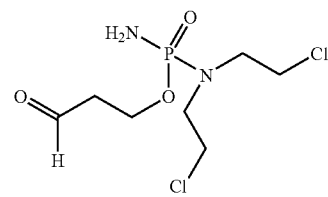

comprising treating said sample to protect the free aldehyde in said compound in the form of a protected aldehyde of the formula:

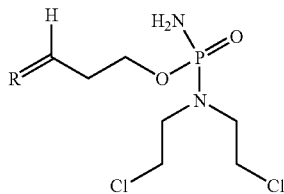

wherein =R forms an aldehyde protecting group, providing a mixture containing 1) said treated sample, 2) an antibody which is substantially selectively reactive with said protected aldehyde and substantially not cross reactive with cyclophosphamide and 3) a conjugate of a carrier with a ligand of the formula:

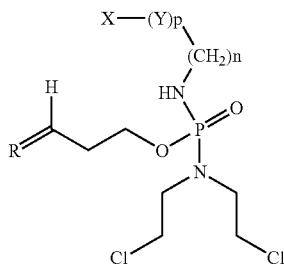

wherein R is as above;
Y is an organic spacing group;
X is a terminal functional group capable of binding to said carrier;
n is an integer of from 1 to 6; and
p is an integer of from 0 to 1,
causing, in said mixture, the protected aldehyde present in said treated sample and said conjugate to bind with said antibody and thereafter measuring the amount of said conjugate in said mixture which is bound to said antibody wherein the presence of the active cyclophosphamide metabolites in the sample can be determined.

2. The immunoassay of claim 1, wherein the sample is a human sample.

3. The immunoassay of claim 2, wherein the antibody is generated from an immunogen comprising an immunogenic polymer linked to said ligand wherein R in the ligand which forms the immunogen and the conjugate and in the protected aldehyde is the same.

4. The immunoassay of claim 3, wherein the antibody is attached to a solid support.

5. The immunoassay of claim 4, wherein the solid support is microtiter plates.

6. The immunoassay of claim 5, wherein the solid support is nanoparticles.

7. The immunoassay of claim 3, wherein the protecting group is a hydrazone whereby =R forms a group of the formula:

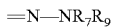

wherein R7 is lower alkyl, phenyl or substituted phenyl; and
R$_9$ is lower alkyl or hydrogen.

8. The immunoassay of claim 7, wherein R$_7$ is 2,4-dinitrophenyl.

9. The immunoassay of claim 3, wherein the protecting group is an oxime so that =R forms a group of the formula

wherein R$_8$ is lower alkyl.

10. An immunoassay for detecting the presence in a sample of a protected cyclophosphamide metabolite of the formula:

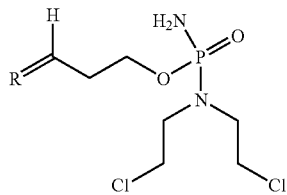

wherein =R forms a protected aldehyde group comprising providing a mixture of said sample, an antibody which is substantially selectively reactive with said protected cyclophosphamide metabolite and not substantially cross-reactive with cyclophosphamide and a conjugate of a carrier with a ligand of the formula:

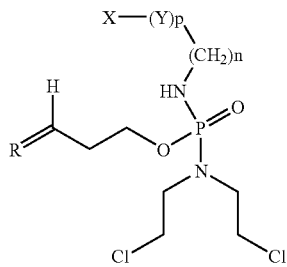

wherein R is as above;
Y is an organic spacing group;
X is a terminal functional group capable of binding to said carrier;
n is an integer of from 1 to 6; and
P is an integer of from 0 to 1,
causing, in said mixture, the protected cyclophosphamide metabolite in said sample and said conjugate to bind with said antibody and thereafter measuring the amount of said conjugate in said mixture which binds to said anfibody whereby the presence of the protected cyclophosphamide metabolite is determined.

11. The immunoassay of claim 9, wherein the sample is taken from a human.

12. The immunoassay of claim 11, wherein the antibody is generated from an immunogen comprising an immunogenic polymer linked to said ligand wherein R in the ligand which forms the immunogen and the conjugate and in the protected aldehyde is the same.

13. The immunoassay of claim 12, wherein the antibody is attached to a solid support.

14. The immunoassay of claim 13, wherein the solid support is microtiter plates.

15. The immunoassay of claim 14, wherein the solid support is nanoparticles.

16. The immunoassay of claim 12, wherein the protecting group is hydrazone whereby =R forms a group of the formula:

$$=N-NR_9R_7$$

wherein $R_7$ is lower alkyl, phenyl or substituted phenyl; and
$R_9$ is hydrogen or lower alkyl.

17. The immunoassay of claim 16, wherein R7 is 2,4-dinitrophenyl.

18. The immunoassay of claim 12, wherein the protecting group is an oxime so that =R forms a group of the formula $$=N-OR_8$$

wherein $R_8$ is lower alkyl.

19. An antibody which substantially selectively binds to a protected aldehyde cyclophosphamide metabolite of the formula:

wherein =R forms an aldehyde protecting group,
while not being substantially cross reactive with cyclophosphamide.

20. The antibody of claim 19, wherein said antibody is derived from an immunogen of an immunogenic polyamine polymer with a ligand of the formula:

wherein R is as above;
Y is an organic spacing group;
X is a terminal functional group capable of binding to a polyamine polymer;
n is an integer of from 1 to 6; and
p is an integer of from 0 to 1.

21. The antibody of claim 20 wherein said antibody is a monoclonal antibody.

22. The antibody of claim 21, wherein said antibody is derived from mice, rabbits, goats, sheep or rats.

23. The antibody of claim 19, wherein the protecting group is hydrazone whereby =R forms a group of the formula:

$$=N-NR_9R_7$$

wherein $R_7$ is lower alkyl, phenyl or substituted phenyl; and
$R_9$ is hydrogen or lower alkyl.

24. The antibody of claim 23, wherein R7 is 2,4-dinitrophenyl.

25. The antibody of claim 19, wherein the protecting group is an oxime so that =R forms a group of the formula:

$$=N-OR_8$$

wherein $R_8$ is lower alkyl.

26. A compound of the formula:

wherein =R forms an aldehyde protecting group;
Y is an organic spacing group;
X is a terminal functional group capable of binding to said carrier;
p is an integer from 0 to 1, and
n is an integer from 1 to 6.

27. The compound of claim 26, wherein p is 0.

28. The compound of claim 27, wherein X is $$-\underset{\underset{O}{\|}}{C}-OR_3, \quad -N=C=R_4, \quad \text{or} \quad -\underset{\underset{O}{\|}}{C}H$$

wherein $R_3$ is hydrogen or taken together with its attached oxygen atom forms a reactive ester and $R_4$ is oxygen or sulfur.

29. The compound of claim 28, wherein X is $$-\underset{\underset{O}{\|}}{C}-OR_3$$

and $R_3$ is hydrogen.

30. The compound of claim 28, wherein X is $$-\underset{\underset{O}{\|}}{C}-OR_3-$$

and $R_3$ forms a reactive ester.

31. The compound of claim 30, wherein the ester formed is a lower alkyl ester, imidoester or amidoester.

32. The compound of claim 26, wherein p is 1.

33. The compound of claim 32, wherein Y is alkylene containing from 1 to 10 carbon atoms, $$-\underset{\underset{O}{\|}}{C}-NH-(CH_2)_m-, \quad \underset{}{\phantom{X}}-(CH_2)_o-,$$

$$-NH-(CH_2)_m-, \quad -NH-\underset{\underset{O}{\|}}{C}-(CH_2)_m- \quad \text{or}$$

$$-\underset{\underset{O}{\|}}{C}-(CH_2)_m- \quad \text{or}$$

$$-NH-\underset{\underset{O}{\|}}{C}-(CH_2)_o-\underset{}{\phantom{X}}-$$

wherein o is an integer from 0 to 6 and m is an integer from 1 to 6.

34. The compound of claim 33, wherein the protecting group is hydrazone whereby =R forms a group of the formula:

$$=N-NR_9R_7$$

wherein $R_7$ is lower alkyl, phenyl or substituted phenyl; and
$R_9$ is hydrogen or lower alkyl.

35. The compound of claim 34, wherein R7 is 2,4-dinitrophenyl.

36. The compound of claim 33, wherein the protecting group is an oxime so that =R forms a group of the formula

wherein $R_8$ is lower alkyl.

37. A conjugate of a carrier with a compound of the formula:

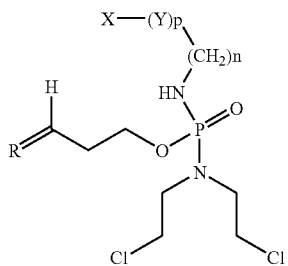

wherein =R forms an aldehyde protecting group;
Y is an organic spacing group;
X is a terminal functional group capable of binding to said carrier;
p is an integer from 0 to 1, and
n is an integer from 1 to 6.

38. The conjugate of claim 37, wherein p is 0.

39. The conjugate of claim 38, wherein X is

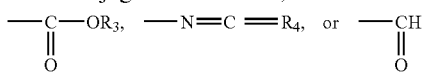

wherein $R_3$ is hydrogen or taken together with its attached oxygen atom forms a reactive ester and $R_4$ is oxygen or sulfur.

40. The conjugate of claim 37, wherein p is 1 and Y is alkylene containing from 1 to 10 carbon atoms,

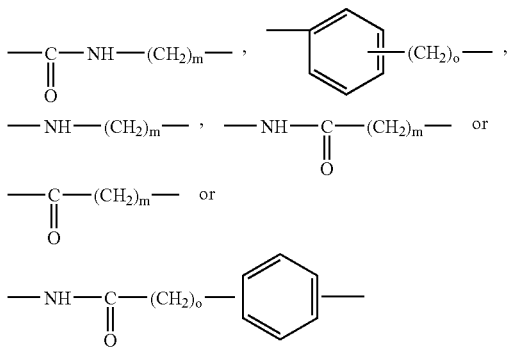

wherein o is an integer from 0 to 6 and m is an integer from 1 to 6.

41. The conjugate of claim 40, wherein the carrier contains one or more amino groups linked by

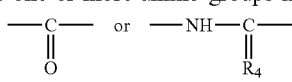

wherein $R_4$ is oxygen or sulfur.

42. The conjugate of claim 37, wherein the protecting group is hydrazone whereby =R forms a group of the formula:

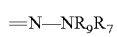

wherein $R_7$ is lower alkyl, phenyl or substituted phenyl; and $R_9$ is hydrogen or lower alkyl.

43. The conjugate of claim 42, wherein $R_7$ is 2,4-dinitrophenyl.

44. The conjugate of claim 37, wherein the protecting group is an oxime and =R forms a group of the formula:

wherein $R_8$ is lower alkyl.

45. The conjugate of claim 37, wherein the carrier is an immunogenic polymer.

46. A kit for determining the presence of active cyclophosphamide metabolites in a patient sample comprising reagents in separate containers, one of the reagents being a conjugate of a carrier with a ligand of the formula:

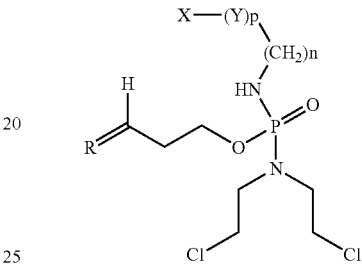

wherein =R forms an aldehyde protecting group;
Y is an organic spacing group;
X is a terminal functional group capable of binding to said carrier;
p is an integer from 0 to 1, and
n is an integer from 1 to 6
and the second container containing an antibody substantially selectively reactive with said ligand and not substantially cross-reactive with cyclophosphamide.

47. The kit of claim 46, wherein said conjugate is present in a predetermined amount in said first container.

48. The kit of claim 47, wherein said kit is used to determine the amount of cyclophosphamide in said sample.

49. The kit of claim 46, wherein said antibody is generated from an immunogen of an immunogenic polyamine polypeptide linked to a compound of the formula:

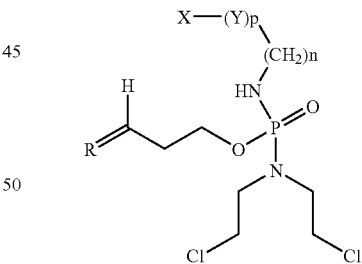

wherein R, n, p, X and Y are as in claim 46 where the aldehyde protecting group R used in the immunogen is the same aldehyde protecting group R used in the conjugate.

50. The kit of claim 49, wherein said kit contains an additional reagent comprising a reactant which reacts with a free aldehyde to form an aldehyde protecting group which protecting group is the same protecting group R as in the ligand which forms the conjugate of claim 46.

* * * * *